US005795632A

United States Patent [19]
Buchalter

[11] Patent Number: 5,795,632
[45] Date of Patent: Aug. 18, 1998

[54] PROTECTIVE COVER SET FOR A MEDICAL PROBE

[75] Inventor: Martin Buchalter, Parsippany, N.J.

[73] Assignee: Parker Laboratories, Orange, N.J.

[21] Appl. No.: 595,918

[22] Filed: Feb. 6, 1996

[51] Int. Cl.[6] .............................. B65D 85/38; G01K 1/08
[52] U.S. Cl. ...................... 428/35.2; 428/35.5; 428/130; 428/192; 428/195; 206/305; 206/363; 383/211; 374/158; 374/209
[58] Field of Search ................... 428/35.2, 35.4, 428/35.5, 195, 192, 122, 130; 128/660.01, 662.06, 736; 374/158, 209; 383/210, 211; 206/484, 484.2, 363, 306, 305

[56] References Cited

U.S. PATENT DOCUMENTS

| | | | |
|---|---|---|---|
| 3,215,265 | 11/1965 | Welin-Berger | 206/306 |
| 3,738,173 | 6/1973 | Sato | 374/158 |
| 3,752,309 | 8/1973 | Hopkins | 206/306 |
| 3,759,370 | 9/1973 | Blatz | 206/306 |
| 4,051,950 | 10/1977 | Järund | 206/306 |
| 4,136,776 | 1/1979 | Poncy | 206/306 |
| 4,614,442 | 9/1986 | Poncy | 374/158 |
| 4,684,018 | 8/1987 | Järund | 206/306 |
| 4,846,344 | 7/1989 | Bala | 206/306 |
| 5,088,834 | 2/1992 | Howe et al. | 128/736 |

*Primary Examiner*—Rena L. Dye
*Attorney, Agent, or Firm*—Whitham, Curtis & Whitham

[57] ABSTRACT

A protective probe cover set for a medical probe designed to be inserted in an endocavity or used interoperatively in an incision of a human or an animal body, comprises a probe cover and a sheath-like outer wrapper. The probe cover consists of flat film material and comprises a mouth for inserting the probe. The outer wrapper consists of two plies being joined along their longitudinal edges. The outer wrapper sheaths at least the length of the cover designed to be inserted in said endocavity. The film material is non sensitizing. Preferably, the probe cover is at least partly filled with a gel which is an excellent transmitter for ultrasound waves and can have lubricating properties, for ease of insertion of the probe into the probe cover, while on the other hand, deterimental effects of air bubbles or the like enclosed between the probe cover and the probe itself are avoided.

28 Claims, 1 Drawing Sheet

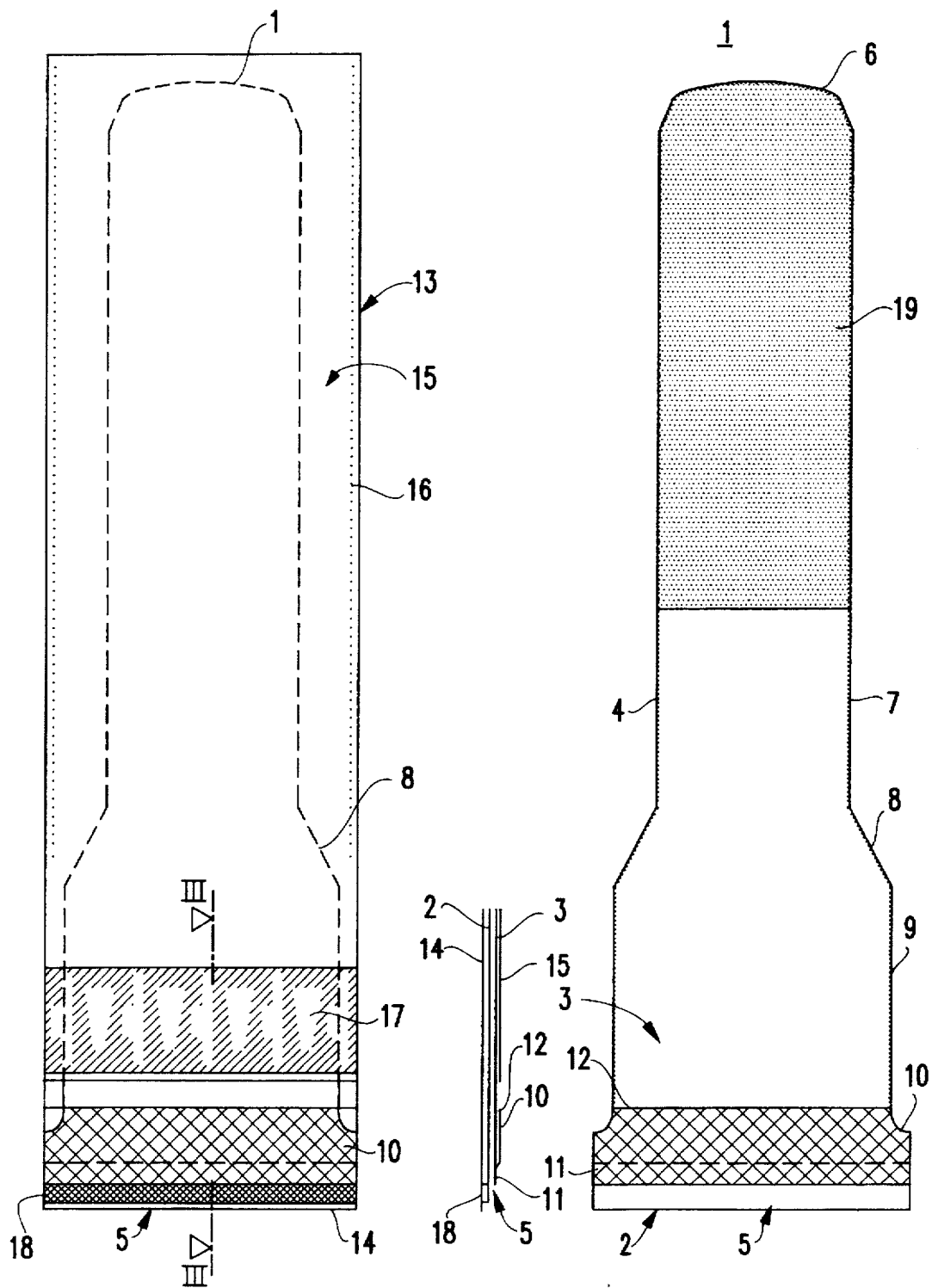

PROTECTIVE COVER SET FOR A MEDICAL PROBE

BACKGROUND OF THE INVENTION

1. Field of the Invention

The present invention relates to a protective cover set for a medical probe designed to be inserted in an endocavity or used interoperatively in an incision of a human or an animal body.

2. Background Description

For medical examinations, often elongated probes must be inserted into body cavities, i.e., endocavities, to position the probe relative to the body area to be examined. One example of such an examination is the insertion of an elongated probe into the vagina for any or all of the following reasons:

Visualize and examine a fetus;

Visualize and examine ovaries;

Visualize and examine a uterus; and

Measure all of the above.

Another example includes rectal insertion of an elongated probe to visualize and examine the prostate gland, polyps, hemorrhoids, etc.

Interoperative ultrasound is an emerging medical technology and, similar to vaginal or rectal procedures, a probe cover is essential. In this example, more than one probe cover size is needed and probe cover sterility is not required. Similar probes and examination procedures also use other principles than reflection of ultrasound; for example, electromagnetic waves of different wave lengths, such as microwaves, infrared waves, visible light, ultra violet radiation, and others.

In all cases, the probe is brought into contact with body tissue or body fluids such as sweat, blood, saliva, mucus, pus or other secretions. Therefore, the probe is contaminated, making it necessary to sterilize the probe before use on the next patient.

Since particularly the comparatively complicated structures of smaller probes comprise smaller openings, a thorough sterilization can be accomplished only with difficulty. To protect the probe against contact with the mentioned body fluids and thereby diminish the danger of transmitting germs or the like from one patient to another, in the past probes have been covered with common condoms designed to contraceptive use. Such condoms are made from natural latex which provides high sensitivity for the user, but compromises strength. However, many patients are allergic to such a material. Furthermore, ultrasound may be noticeably attenuated by a condom covering an ultrasound probe or transducer, particularly by air bubbles trapped between the condom and the probe unless it is carefully gelled inside. In many endocavity procedures, two and perhaps three condoms are used. The air space between each condom must be gelled. Furthermore, handling of the traditionally packed, i.e., rolled, condoms proved to be inconvenient for the intended use in hospitals.

SUMMARY OF THE INVENTION

One object of the invention is to develop a protective probe cover set for a medical probe, whereby a suitable probe cover provides for tidiness of the probe itself during use of the probe. During storage, the probe cover set must be protected against contamination emanating from the hospital environment.

Another object of the invention is to facilitate handling and preparation of an elongated medical probe before insertion into an endocavity.

In accomplishing the foregoing objects, there has been provided, according to the present invention, a protective cover set for a medical probe designed to be inserted in an endocavity or used interoperatively in an incision of a human or an animal body, which comprises: a probe cover, said probe cover in turn being covered by a sheath-like outer wrapper, said probe cover consisting of flat film material and comprising a mouth for inserting said probe, said outer wrapper consisting of two plies being joined along their longitudinal edges, said outer wrapper sheathing at least the length of said cover designed to be inserted in said endocavity. The film material is non sensitizing.

In a preferred embodiment, the probe cover is at least partly filled with a gel which is an excellent transmitter for ultrasound waves and can have lubricating properties, for ease of insertion of the probe into the probe cover, while on the other hand, detrimental effects of air bubbles or the like enclosed between the probe cover and the probe itself are avoided.

According to preferred dimensions, the probe cover is essentially of constant width except for an outward tapering section comprising said mouth and the outer wrapper is of constant width, too, and width being equal to the greatest width of said probe cover.

To facilitate production, the two plies forming the sheath-like outer wrapper need not be joined to each other along a shorter edge opposing said mouth.

The probe cover can either be made of a single sheet of flat film material which is being folded to form two plies or the probe cover can be made of two sheets of flat film material which are both cut in shape and placed on top of each other to form two plies, whereby in either case the two plies are joined together along adjacent edges, except for a short section of those adjacent edges forming said mouth.

In order to make the opening of the cover set easier, said outer edges of the two plies forming the outer wrapper can be joined together in a manner so that the resulting joint provides for low retention forces as compared to the tensile strength of the probe cover.

To avoid displacement of the probe cover inside the outer wrapper, at least one of the two plies of the probe cover can be fixed in a separable manner to the adjacent one of the plies forming the outer wrapper.

The probe cover can be fixed inside the outer wrapper by means of an adhesive agent.

A preferred embodiment furthermore comprises an outer wrapper whereby one of the two plies forming said outer wrapper forms an upper ply while the other of said two plies forms a lower ply, said upper ply being shorter than said lower ply, thereby leaving the section adjacent to the mouth of the probe cover uncovered. Thus, grasping the mouth of the probe cover is made easier.

The flat film material of which the probe cover is made can be polyethylene-copolymer, preferably transparent polyethylene-copolymer. Preferably, the various joints can be formed by heat sealing to provide for a inexpensive manufacturing.

In a preferred embodiment, the mouth portion of the probe cover is optically marked so that opening of the mouth is facilitated. Likewise, the upper of the two plies forming the outer wrapper can be transparent and the lower ply can be optically distinguished from said upper ply, so that the probe cover is better visible.

A preferred embodiment furthermore comprises a strip of plastic film material which is fixed to the upper ply of the probe cover, thereby forming a pocket-like handle near said mouth of the probe cover. Thus grasping and opening of the mouth portion of the probe cover is made easier. The strip forming the pocket-like handle is preferably made of colored plastic material to further improve handling of the inventive cover set.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a plan view of a probe cover according to the invention consisting of two plies of flat film material;

FIG. 2 is a plan view of the probe cover of FIG. 1 in turn being covered by a sheath-like outer wrapper; and FIG. 3 is a cross-sectional view taken along line III—III in FIG. 2 showing the construction of the cover set.

DETAILED DESCRIPTION OF A PREFERRED EMBODIMENT OF THE INVENTION

Referring now to the drawings, and more particularly to FIG. 1, there is shown the probe cover 1 consisting of an lower ply 2 made of flat film material and a upper ply 3 of flat film material, which are cut into a suitable shape and joined together along their edges by means of a heat sealed seam 4. The heat sealed seam 4 does not extend into the area of the mouth 5 which is located on one end of the elongated probe cover 1. The shape of the probe cover is of constant width including a closed end 6, the area of constant width being defined by two essentially straight parallel edges 7.

An outwardly tapering section 8 leads to a wider section 9 adjacent to mouth 5. The wider section 9 facilitates insertion of a probe into probe cover 1. The heat sealed seam 4 extends along the edges of the wider section 9 up to shortly before mouth 5, so that the two plies 2, 3 are not fixed to each other in the area shortly before the mouth 5, thereby making a separation of the two plies easier in order to form a funnel-like mouth. Both plies are made from a transparent polyethylene film material. The upper ply is slightly shorter and comprises a white colored strip 10 which is fixed to the upper ply 3 by means of a heat sealed seam 11 and by means of the heat sealed seam 4 together with the lateral edges of the two plies 2 and 3.

Edge 12 opposing mouth 5 is not fixed to upper ply 3 so that strip 10 forms a pocket which can be grasped with a finger thereby making separation of upper ply 3 and lower ply 2 for creating a funnel-like mouth easier, thus causing the two plies to break away, leaving the probe ready to use.

Also, FIG. 1 shows that probe cover 1 is filled with a gel layer 19, extending from closed end 6 over approximately half the length of the probe cover 1. Gel 19 is a good conductor for ultrasound waves and fills the space remaining between the probe cover and the probe itself, thereby avoiding the detrimental effects of air bubbles enclosed between the probe cover and the probe. Thus, the efficiency of the ultrasound probe or transducer covered by probe cover 1 is not diminished.

FIG. 2 shows probe cover 1 in turn being covered by an outer sheath-like wrapper 13. Wrapper 13 consists of a flat lower ply 14 and an upper ply 15. The two plies 14 and 15 are fixed to each other along their lateral edges by means of adhesive joints 16, whereby the adhesive is applied only up to the tapering section 8 of probe cover 1. Upper ply 15 is shorter than lower ply 14 and therefore ends before strip 10 of probe cover 1. The upper ply 15 is transparent and bears a colored mark in the form of a stripe 17 to be optically distinguishable.

FIG. 2 shows that probe cover 1 rests on lower ply 14 in the area adjacent to mouth 5; however, it is uncovered in an upper direction because upper ply 15 is shorter, so that strip 10 can be easily grasped for opening mouth 5 without removing the outer wrapper completely or partly.

FIG. 2 furthermore shows lower ply 2 of probe cover 1 being fixed to lower ply 14 of outer wrapper 13 by means of an adhesive joint 18 extending over the entire width of lower ply 14.

The ply construction in the area of mouth 5 is furthermore shown in FIG. 3. FIG. 3 shows particularly adhesive joint or strip 18 fixed to the lower ply 2 of probe cover 1 and to the lower ply 14 of outer wrapper 13. Furthermore, heat sealed seam 11 can be seen, between upper ply 3 of probe cover 1 and the strip 10 designed to lift the upper ply 3 from the lower ply 2.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A protective cover set for a medical probe designed to be inserted in an endocavity or used interoperatively in an incision of a human or an animal body, said cover set comprising:

a probe cover made from a film material having a mouth for inserting said probe; and an outer wrapper formed from two plies joined along adjacent longitudinal edges, said outer wrapper being joined to said probe cover by an adhesive, said outer wrapper covering at least a length of said probe cover.

2. The probe cover set claimed in claim 1, wherein said probe cover is at least partly filled with a gel.

3. The probe cover set as claimed in claim 1, wherein said probe cover is essentially of constant width except for an outward tapering section comprising said mouth.

4. The probe cover set as claimed in claim 3, wherein said outer wrapper is of constant width, said width being equal to a greater width of said probe cover.

5. The probe cover set as claimed in claim 1, wherein said two plies of said outer wrapper are not joined to each along an edge opposing said mouth of said probe cover.

6. The probe cover set as claimed in claim 1, wherein said probe cover is made of a single sheet of flat film material, said sheet being folded to form two plies, said plies being joined together along adjacent longitudinal edges.

7. The probe cover set as claimed in claim 6, wherein at least one of said plies of said probe cover is fixed in a separable manner to the adjacent one of said plies of said outer wrapper.

8. The probe cover set as claimed in claim 1, wherein said probe cover is made of two sheets of flat film material, said sheets being cut in shape and being placed on top of each other to form two plies, said plies being joined together along adjacent edges, except for a short section of said adjacent edges forming said mouth.

9. The probe cover set as claimed in claim 8, wherein at least one of said plies of said probe cover is fixed in a separable manner to the adjacent one of said plies of said outer wrapper.

10. The probe cover set as claimed in claim 1, wherein one of said plies of said outer wrapper forms an upper ply while the other of said two plies forms a lower ply, said upper ply being shorter than said lower ply, thereby leaving a section adjacent to said mouth of said probe cover unsheathed.

11. The probe cover set as claimed in claim 1, wherein said film material is transparent.

12. The probe cover set as claimed in claim 1, wherein said film material consists of a copolymer of polyethylene.

13. The probe cover set as claimed in claim 1, wherein said probe cover is made of a single sheet of flat film material, said sheet being folded to form two plies, said plies being joined together along adjacent longitudinal edges, said joint being formed by heat sealing.

14. The probe cover set as claimed in claim 1, wherein said probe cover is made of two sheets of flat film material, said sheets being cut in shape and being placed on top of each other to form two plies, said plies being joined together along adjacent edges, except for a short section of said adjacent edges forming said mouth, said joint being a heat sealed joint.

15. The probe cover set as claimed in claim 1, wherein said mouth of said probe cover bears a colored edge marker.

16. The probe cover set as claimed in claim 1, wherein an upper one of said two plies forming said outer wrapper is transparent and a lower one of said two plies can be optically distinguished from said upper one of said two plies.

17. The probe cover set as claimed in claim 1, wherein an upper one of said two plies forming said outer wrapper is transparent and a lower one of said two plies can be optically distinguished from said upper one of said two plies, and wherein a short edge of said transparent upper ply is marked with a colored stripe to be optically distinguishable.

18. The probe cover set as claimed in claim 1, further comprising a strip of plastic film material, said strip being fixed to an upper ply of said probe cover, thereby forming a handle near said mouth of said probe cover.

19. The probe cover set as claimed in claim 1, wherein said probe cover is formed from an upper ply and a lower ply joined together and further comprising a strip of plastic film material fixed to said upper ply of said probe cover, thereby forming a handle near said mouth of said probe cover, and wherein said upper and lower plies of said probe cover are of transparent material and said strip is made of a colored plastic material.

20. A protective cover for a medical probe, comprising:
an upper ply side and a lower ply side, said upper ply side and said lower ply side each having side edges a top and a bottom, said side edges and said bottom of said lower ply side being joined to said side edges and bottom of said lower ply side with said top of said upper ply side offset from said top of said lower ply side, said upper ply side and said lower ply side defining an inner volume bounded by said side edges and said bottom for sheathing a medical probe, and a mouth defined by said top of said upper ply side and said top of said lower ply side for accessing said inner volume; and a strip of material having a top edge, a bottom edge, and two lateral edges, said strip of material being connected to said top of said upper ply at said top edge and said two lateral edges with said bottom edge being positioned outside said inner volume wherein said strip of material and said top of said upper ply define a pocket to be grasped by a finger.

21. The protective cover recited in claim 20 further comprising a gel positioned within said inner volume.

22. The protective cover recited in claim 21 wherein said upper ply and said lower ply are separate pieces of material, and further comprising a joining means for joining said bottom of said upper ply to said bottom of said lower ply.

23. The protective cover recited in claim 21 wherein said upper ply and said lower ply are constructed from a contiguous piece of material.

24. A protective cover set for a medical probe designed to be inserted in an endocavity of used interoperatively in an incision of a human or an animal body, said cover set comprising:

a probe cover made from a film material having a mouth for inserting said probe;

an outer wrapper formed from two plies joined along longitudinal edges, said outer wrapper being joined to said probe cover and covering at least a length of said probe cover; and a strip of material having a top edge, a bottom edge, and two lateral edges, said strip of material being connected to said mouth of said probe cover at said top edge and said two lateral edges but not at said bottom edge so as to define a pocket to be grasped by a finger.

25. A protective cover set for a medical probe designed to be inserted in an endocavity or used interoperatively in an incision of a human or an animal body, said cover set comprising:

a probe cover made form a film material having a mouth for inserting said probe;

an outer wrapper formed from two plies covering at least a length of said probe cover; and a joint formed along longitudinal edges of said two plies of said outer wrapper formed in a manner that provides for low retention forces as compared to a tensile strength of said probe cover.

26. The protective cover set recited in claim 25 wherein said two plies of said outer wrapper are not joined to each other along a shorter edge opposing said mouth.

27. The protective cover set recited in claim 25 further comprising a strip of material having a top edge, a bottom edge, and two lateral edges, said strip of material being connected to said mouth of said probe cover at said top edge and said two lateral edges but not at said bottom edge so as to define a pocket to be grasped by a finger.

28. The protective cover set recited in claim 25 wherein said outer wrapper is joined to said probe cover.

* * * * *